United States Patent [19]
Warrellow et al.

[11] Patent Number: 5,859,034
[45] Date of Patent: Jan. 12, 1999

[54] TRI-SUBSTITUTED PHENYL COMPOUNDS WHICH HAVE USEFUL PHARMACEUTICAL ACTIVITY

[75] Inventors: Graham John Warrellow, Middlesex; Julien Alistair Brown, Berkshire, both of United Kingdom

[73] Assignee: Celltech Therapeutics, Limited, United Kingdom

[21] Appl. No.: 984,198

[22] Filed: Dec. 3, 1997

[30] Foreign Application Priority Data

Dec. 4, 1996 [GB] United Kingdom .................. 9625184

[51] Int. Cl.⁶ ............... C07D 213/02; C07D 237/06; A61K 31/44; A61K 31/415
[52] U.S. Cl. ................. 514/357; 514/247; 514/255; 514/256; 514/396; 544/224; 544/242; 544/336; 546/330; 546/332; 548/335.1; 548/335.5; 548/336.1
[58] Field of Search ................. 544/224, 242, 544/336; 546/330, 332; 548/335.1, 335.5, 336.1; 514/247, 255, 256, 357, 396

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,271,002 | 12/1993 | Hawkins | 514/252 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow et al. | 514/336 |
| 5,693,659 | 12/1997 | Head et al. | 514/357 |
| 5,723,460 | 3/1998 | Warrellow et al. | 514/247 |
| 5,739,144 | 4/1998 | Warrellow et al. | 514/277 |

FOREIGN PATENT DOCUMENTS

| | | |
|---|---|---|
| 0 223 461 A2 | 8/1987 | European Pat. Off. . |
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 2 545 356 A1 | 11/1984 | France . |
| 250 1443 | 7/1975 | Germany . |

(List continued on next page.)

OTHER PUBLICATIONS

Yamaguchi et al., Chemical Abstracts, vol. 110, No. 11, Abstract No. 94,706Z, p. 655, Mar. 13, 1989.

Kefalas, P. et al., "Signalling by the p60$^{c-src}$ Family of Protein–Tyrosine Kinases", *Int. J. Biochem. Cell Biol.*, 1995, 27(6), 551–563.

Chatterjee, A. et al., "Total Synthesis of Ring–c Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49 (4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

(List continued on next page.)

*Primary Examiner*—Zinna Northington Davis
*Attorney, Agent, or Firm*—Woodcock Washburn Kurtz Mackiewicz & Norris LLP

[57] ABSTRACT

Tri-substituted phenyl derivatives having the general formula (I):

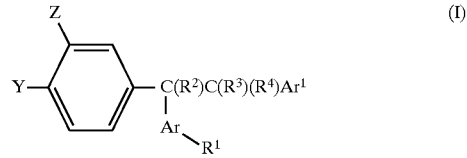

In a preferred embodiment, Y is preferably an —$XR^a$ group, X is preferably —O—, Z is preferably an —$XR^5$ group, $R^a$ is preferably hydrogen or an optionally substituted alkyl group, $R^1$ is preferably an —NHC(—NCN)NHR$^{13}$ or —NHC(=CHNO$_2$)NHR$^{13}$ group, $R^2$, $R^3$ and $R^4$ are preferably hydrogen, $R^5$ is preferably an optionally substituted alkyl, alkenyl, cycloalkyl, cycloalkenyl or heterocycloalkyl group, $R^{12}$ is preferably hydrogen or a $C_{1-3}$alkyl group, $R^{13}$ is preferably hydrogen, a $C_{1-3}$alkyl group, an optionally substituted phenyl group or an optionally substituted phenyl$C_{1-3}$alkyl group, Ar$^1$ is preferably an optionally substituted nitrogen containing heteroaryl group, and Ar is preferably a phenyl group. Compounds of the invention are potent and selective phosphodiesterase type IV inhibitors and are useful in the prophylaxis and treatment of various diseases, such as asthma, which are associated with an unwanted inflammatory response or muscular spasm.

16 Claims, No Drawings

FOREIGN PATENT DOCUMENTS

| | | |
|---|---|---|
| 3-77872 | 4/1991 | Japan . |
| 3-77923 | 4/1991 | Japan . |
| 1588639 | 4/1981 | United Kingdom . |
| 87/06576 | 11/1987 | WIPO . |
| 91/15451 | 10/1991 | WIPO . |
| 91/16892 | 11/1991 | WIPO . |
| 92/00968 | 1/1992 | WIPO . |
| 92/06085 | 4/1992 | WIPO . |
| 92/06963 | 4/1992 | WIPO . |
| 92/07567 | 5/1992 | WIPO . |
| 92/12961 | 8/1992 | WIPO . |
| 92/19594 | 11/1992 | WIPO . |
| 92/19602 | 11/1992 | WIPO . |
| 93/10118 | 5/1993 | WIPO . |
| 93/19748 | 10/1993 | WIPO . |
| 94/02465 | 2/1994 | WIPO . |
| 94/10118 | 5/1994 | WIPO . |
| 94/12461 | 6/1994 | WIPO . |
| 94/13661 | 6/1994 | WIPO . |
| 94/14742 | 7/1994 | WIPO . |
| 94/20446 | 9/1994 | WIPO . |
| 94/20455 | 9/1994 | WIPO . |
| 95/09847 | 4/1995 | WIPO . |
| 95/09851 | 4/1995 | WIPO . |
| 95/09852 | 4/1995 | WIPO . |
| 95/09853 | 4/1995 | WIPO . |
| 95/17386 | 6/1995 | WIPO . |
| 95/31451 | 11/1995 | WIPO . |
| 95/33727 | 12/1995 | WIPO . |
| 95/35281 | 12/1995 | WIPO . |
| 95/35283 | 12/1995 | WIPO . |
| 96/14843 | 5/1996 | WIPO . |
| 97/09297 | 3/1997 | WIPO . |

OTHER PUBLICATIONS

Degani, I. et al., "Cationi etero–aromatici Nota VI — Sintesi di alcuni derivati del perclorato di tiaccromilio", *Boll. Sci. Fac. Chim. Ind. Bologna*, 1996, 24 (2–3) , 75–91 (English Summary Only).

Geissler et al., "Biochemical and Biological Activity of a Novel Class of Tyrosine Protein Kinase Inhibitors", *J. Biol. Chem.*, 1990, 265 (36) , 22255–22261.

Griffin, R.W. et al., "1–Methyl–7–halo–2–naphtalenecarboxylic Acid Derivatives", *J. Organic Chem.*, 1964, 29 (8), 2109–2116.

Gupta, A.S. et al., "Friedel–Crafts Condensation of Ethyl Allylmalonate with Anisole", *Tetrahedron*, 1967, 23 , 2481–2490.

Hart et al., "Alkylation of Phenol with a Homoallylic Halide", *J. Am. Chem. Soc.*, 1963, 85 , 3269–3273.

Johnson et al., "Identification of Retinoic Acid Receptor β Subtype Specific Agonists", *J. Med. Chem.*, 1996, 39 (26) , 5027–5030.

Lehmann, J. et al., "Lactones; XIII. Grignard Reaction Followed by Phase–Transfer Oxidation: A Convenient Synthesis of γ, γ–Distributed γ–Butyrolactones from γ–Butyrolactone", *Synthesis*, 1987, 1064–1067 (English abtract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Ashton, "Selective Type IV Phosphodiesterase Inhibitors as Antiasthmatic Agents. The Syntheses and Biological Activites of 3–(Cyclopentyloxy)–4–methyoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of ω, ω–Diarylacetophenones Aminated in the Aromatic Nucleus. Plynitration of Triarylethylenes", *Chem. Abstr.*, 1964, 61 (13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chemical Abstracts, "Hypoglycemic Pharmaceuticals Containing Manzammide Derivatives", *Chem. Abstr.*, 1983, 99(6), No. 43558Z.

Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3, 1985.

Daves, G.D. et al., "Pyrimidines. XIII. 2–and 6–Substituted 4–Pyrimidinecarboxylic Acids", *J. Of Hev. Chem.*, 1964, 1, 130–133.

Dietl, F. et al., "Chinone von Benzo–und Dibenzokronenethern", *Synthesis*, 1985, 626–631.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

El–Wakil et al., "Study of the proton magnetic resonance of methoxythamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. of Biol. Chem.*, 1990, 265 (36), 22255–22261.

Grammaticakis, "Contribution A L'Etude de L'Absortion Dans L'Ultraviolet Moyen Et Le Visible des N–Aroyl–Arylamines. IV. 2, 3–, 3,4–et 2, 4–, dimethoxybenzolylarylamines", *Bulletin DeLa Societa Chemique De France*, 1965, 848–858.

Green and Wuts, "Protective Group in Organic Synthesis", John Wiley & Sons, New York, 1991.

Hanks, S.K. et al., "The eukaryotic protein kinase superfamily: Kinase (catalytic) domain structure and classification", *FASEB J.*, 1995, 9, 576–596.

Heaslip et al., "Phosphodiesterase–IV Inhibition, Respiratory Muscle Relaxation and Bronchodilation by WAY–PDA–641", *J. Pharm. Exper. Ther.*, 1993, 268 (2), 888–896.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4 (2), 123–132.

Karlsson et al., "T–Lymphocyte and Inflammatory Cell Research in Asthma", Joller, G. et al. (eds.) , Academic Press, 1993, 323–347.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–K$_m$3 Rolipram–Sensitive Cyclic AMP Phosphodiesterase", *Molecular and Cellular Biol.* 1990, 10 (6), 2678–2686.

Manhas et al., "heterocyclic Compounds XII. Quinazoline Derivatives as Potential Antifertility Agents (1)" *J. Heterocyclic Chem.*, 1979, 16, 711–715.

Mathison et al., "Synthesis and Hypotensive Properties of Tetrahydroixoquinolines", *J. Med. Chem.*, 1973, 16 (4), 332–336.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39 (18), 2787–2793.

Mezheritskaya, "Synthesis and properties of carboxonium het=erocyclic systems. VII. Synthesis and properties of 2–benzyl–substituted 1, 3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Miyaura, N. et al., "the Palladium–Catalyzed Cross–Coupling Reaction of Phenylboronic Acid with Haloarenes in the Presence of Bases", *Synth. Comm.*, 1981, 11, 513–519.

Newton, A.C., "Protein Kinase C: Structure, Function, Regulation", *J. Biol. Chem.*, 1995, 270 (48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxpropenylbenzene at a rotating platinum electrode in unbuffered acetonitrile and in acetonitrile–pyridine solution" *Chem. Abstr.*, 1964, 60 (8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Porter et al., "Preparation of 6–phenyl–3–(5–tetrazolyl) pyridin–=2(H)–one Derivatives as Cyclic AMP–dependent protein kinase Agonists" *Chem. Abstr.*, 1992, 117 (9), 90296n.

Ramalingam, Deshmukh and Sattur, "Synthesis and Pharmacology of 2, 5–Disubstituted 1,3,4–Zxadiazoles" *J. Indian Chem. Soc.*, 1981, 58 (3), 269–271.

Reddy et al., "Inhibition of Breast Cancer Cell Growth in Vitro by a Tyrosine kinases Inhibitor" *Cancer Research*, 1992, 52, 3636–3641.

Sakakibara, K. et al., "Preparation of N–pyridyl–4–(benzyloxy) benzamides as Cardiotonics", *Chem. Abstr.*, 1988, 108, No. 131583p.

Sánchez, H.I. et al., "Formal Total Syntehsis of β–Pipitzol", *Tetrahedron*, 1985, 41 (12), 2355–2359.

Schneider et al., "Catechol Estrogens of the 1,1, 2–Triphenylbut–1–ene Type: Relationship Between Structure, Estradiol Receptor Affinity, Estrongenic and Antiestrogenic Properties, and Mammary Tumor Inhibiting Acivities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilyation; General Synthesis of Unsymmetrical iphenyls and n–Terphenyls", *Tetrahedron Lett.*, 1987, 28 (43), 5093–5096.

Shioiri et al, "New Methods and Reagents in Organic Synthesis. 3. Diethyl Phosphorocyanidate: A new Reagent for C–Acylation", *J. Org. Chem.*, 1978, 43, 3631–3632.

Yoneda et al., "The Antiproliferative Effects of Tyrosine Kinase Inhibitors Tyrphostins on a Human Squamous Cell Carcinoma in Vitro and In Nude Mice" *Cancer Research*, 1991, 51, 4430–4435.

Thompson, W. J. and Gaudino, J., "A General Synthesis of 5–Arylnicotinates" *J. Org. Chem.*, 1984, 49, 5237–5243.

Tominega et al., "Polarized Ethylenes. IV. Synthesis of Polarized Ethylenes Using Thioamides and Methyl Dithiocarboxylates and Their Application to Syntheses of Pyrazoles, Pyrimidines, Pyrozolo [3, 4–d] pyrimidines, and 5–Aza [2.3.3] cyclazines", *J. Het. Chem.*, 1990, 27, 647–660.

Trost and Fleming (ed.), Comprehensive Organic Synthesis, Pergamon Press, New York, 1991, 3, 531–541.

Tsutsumi, K. et al., "Preparation of (Dialkoxyphosphinoyl-methyl) benzamides as Antihyperlipidemics", *Chem. Abstr.*, 1990, 113, No. 6599a.

Vidal et al., "Electrophilic Amination: Preparation and Use of N–Boc–3–(4–cyanophenyl) oxaziridine, a New Reagent That Transfers a N–Boc Group to N–and C–Nucleophiles", *J. Org. Chem.*, 1993, 58, 4791–4793.

Yeadon et al., "Mechanisms Contributing to Ozone–Induced Bronchial Hyperreactivity in Guinea Pigs", *Pulmonary Pharm.*, 1992, 5, 39–50.

TRI-SUBSTITUTED PHENYL COMPOUNDS WHICH HAVE USEFUL PHARMACEUTICAL ACTIVITY

This invention relates to a novel series of triarylethanes, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11:150–155 and Nicholson et al (1991) TIPS, 12:19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

In our International Patent Specifications Nos. WO 94/14742, WO 95/35281 and WO 95/35283 we describe triarylethanes which are potent inhibitors of the PDE IV isoenzyme at concentrations at which they have little or no inhibitory action on other PDE isoenzymes. The compounds are of use in medicine, especially in the prophylaxis and treatment of asthma.

We have now found a particular series of triarylethanes which are potent and selective PDE IV inhibitors and which also have other advantageous pharmacological properties, including especially improved metabolic stability.

Thus according to one aspect of the invention, we provide a compound of formula (1)

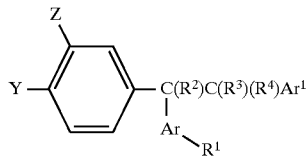

(1)

wherein

Y is a halogen atom, or a —$XR^a$ group where X is —O—, —$S(O)_m$— [where m is zero or an integer of value 1 or 2], or —$N(R^b)$— [where $R^b$ is a hydrogen atom or an optionally substituted alkyl group] and $R^a$ is a hydrogen atom or an optionally substituted alkyl group;

Z is a group —$XR^5$ [where $R^5$ is an optionally substituted alkyl, alkenyl, cycloalkyl, cycloalkenyl or heterocycloalkyl group], —$C(R^6)$=$C(R^7)(R^8)$ [where $R^6$ is a hydrogen or fluorine atom or a methyl group, and $R^7$ and $R^8$, which may be the same or different, is each a hydrogen or fluorine atom or an optionally substituted alkyl, alkenyl, alkoxy, alkylthio, —$CO_2R^9$ [where $R^9$ is a hydrogen atom or an optionally substituted alkyl, aralkyl or aryl group], —$CONR^{10}R^{11}$ [where $R^{10}$ and $R^{11}$, which may be the same or different, is each as defined for $R^9$], —$CSNR^{10}R^{11}$, —CN or —$NO_2$ group, or $R^7$ and $R^8$ together with the carbon atom to which they are attached are linked to form an optionally substituted cycloalkyl, cycloalkenyl or heterocycloalkyl group] or -[—$CH(R^6)$]$_n$$CH(R^7)(R^8)$ where n is zero or the integer 1;

$R^2$ is a hydrogen or a fluorine atom, an optionally substituted alkyl group, or a hydroxyl group;

$R^3$ is a hydrogen or a fluorine atom, or an optionally substituted alkyl group;

$R^4$ is a hydrogen or a fluorine atom, an optionally substituted alkyl group or an $OR^c$ group where $R^c$ is a hydrogen atom or an optionally substituted alkyl or alkenyl group, or an alkoxyalkyl, alkanoyl, formyl, carboxamido or thiocarboxamido group;

$Ar^1$ is an optionally substituted monocyclic or bicyclic aryl group, optionally containing one or more heteroatoms selected form oxygen, sulphur or nitrogen atoms;

Ar is a monocyclic or bicyclic aryl group, optionally containing one or more heteroatoms selected from oxygen, sulphur or nitrogen atoms;

$R^1$ is a group —$N(R^{12})C$(=NCN)$NHR^{13}$ [where $R^{12}$ is a hydrogen atom or a $C_{1-3}$-alkyl group and $R^{13}$ is a hydrogen atom, a $C_{1-3}$alkyl group or an optionally substituted phenyl or phenyl$C_{1-3}$alkyl group], —$N(R^{12})C$(=NCN)$SR^{13}$, $N(R^{12})C$(=$CHNO_2$)$NHR^{13}$ or —$N(R^{12})C$(=$CHNO_2$)$SR^{13}$; and the salts, solvates, hydrates, prodrugs and N-oxides thereof.

It will be appreciated that certain compounds of formula (1) may have one or more chiral centres, depending for example on the nature of the groups Z, $R^2$, $R^3$ and $R^4$. Where one or more chiral centres is present, enantiomers or diastereomers may exist, and the invention is to be understood to extend to all such enantiomers, diastereomers and mixtures thereof, including racemates. The compounds of the invention also exist as geometric isomers and the invention is to be understood to extend to all such isomers and mixtures thereof.

In the compounds of formula (1), when Y is a halogen atom it may be for example a fluorine, chlorine, bromine or iodine atom.

$R^a$ in the compounds of formula (1) may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example —$CH_2F$, —$CH_2Cl$, —$CHF_2$, —$CHCl_2$, —$CF_3$ or —$CCl_3$ groups.

In compounds of formula (1), X may be an oxygen or a sulphur atom, or a group —$S(O)$—, —$S(O)_2$—, —NH— or $C_{1-6}$alkylamino, for example a $C_{1-3}$ alkylamino, e.g. methylamino [—$N(CH_3)$-] or ethylamino [—$N(C_2H_5)$-] group.

Alkyl groups represented by $R^5$, $R^7$ or $R^8$ in the compounds of formula (1) include optionally substituted straight or branched $C_{1-6}$alkyl groups. Particular examples include $C_{1-3}$alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$alkoxy e.g. $C_{1-3}$alkoxy such as methoxy or ethoxy or —$CO_2R^9$, —$CONR^{10}R^{11}$, —$CSNR^{10}R^{11}$ or —CN groups. Particular examples of substituted alkyl groups include —$CH_2F$, —$CH_2Cl$, —$CHF_2$, —$CHCl_2$, $CF_3$ or —$CCl_1$ groups.

Alkenyl groups represented by $R^5$, $R^7$ or $R^8$ in the compounds of formula (1) include optionally substituted straight or branched $C_{2-6}$alkenyl groups optionally interrupted by one or more —O—, —S(O)$_m$— and/or —N($R^b$)— atoms or groups. Particular examples include ethenyl, propen-1-yl and 2-methylpropen-1-yl groups. Optional substituents include those described above in relation to alkyl groups represented by the groups $R^5$, $R^7$ or $R^8$.

When $R^7$ or $R^8$ in compounds of formula (1) is an alkoxy or alkylthio group it may be for example an optionally substituted straight or branched $C_{1-6}$ alkoxy or $C_{1-6}$alkylthio group optionally interrupted by one or more —O—, —S(O)$_m$— and/or —N($R^b$)— atoms or groups. Particular examples include $C_{1-3}$alkoxy, e.g. methoxy or ethoxy, or $C_{13}$alkylthio e.g. methylthio or ethylthio groups. Optional substituents include those described above in relation to alkyl groups represented by the groups $R^7$ or $R^8$.

When $R^5$ is, or $R^7$ and $R^8$ together with the carbon atom to which they are attached are, a cycloalkyl or cycloalkenyl group, the group may be for example a $C_{3-8}$cycloalkyl group such as a cyclobutyl, cyclopentyl, or cyclohexyl group or a $C_{3-8}$ cycloalkenyl group containing for example one or two double bonds such as a 2-cyclo-buten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each of said groups being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups. Examples of heterocycloalkyl groups represented by $R^5$, and $R^7$ and $R^8$ together, include $C_{3-8}$-heterocycloalkyl groups such as tetrahydrofuranyl or pyrrolidinyl groups. Such groups may be substituted by one, two or three substituents as just described for cycloalkyl and cycloalkenyl groups represented by $R^5$, $R^7$ and $R^8$.

When $R^7$ or $R^8$ is a —CO$_2$R$^9$, —CONR$^{10}$R$^{11}$ or CSNR$^{10}$R$^{11}$ group or such a group is present as a substituent in compounds of formula (1) it may be for example a —CO$_2$H, —CONH$_2$ or —CSNH$_2$ group or a group —CO$_2$R$^9$ —CONR$^{10}$R$^{11}$, —CSNR$^{10}$R$^{11}$, —CONHR$^{11}$, or —CSNHR$^{11}$ where $R^9$, $R^{10}$ and $R^{11}$ where present is a Cl-$_3$alkyl group such as methyl or ethyl group, a $C_{6-12}$aryl group, for example an optionally substituted phenyl, or a 1- or 2-naphthyl group, or a $C_{6-12}$aryl$C_{1-3}$alkyl group such as an optionally substituted benzyl or phenethyl group. Optional substituents which may be present on these aryl groups include $R^{16}$ substituents discussed below in relation to the group Ar$^1$.

When the group $R^4$ in compounds of formula (1) is an OR$^c$ group it may be for example a hydroxyl group or a group —OR$^c$ where R$^c$ is an optionally substituted straight or branched $C_{1-6}$alkyl group, e.g. a $C_{1-3}$alkyl group such as a methyl or ethyl group, a $C_{2-6}$alkenyl group such as an ethenyl or 2-propen-1-yl group, a $C_{1-3}$alkoxy$C_{1-3}$alkyl group such as a methoxymethyl, ethoxymethyl or ethoxyethyl group, a $C_{1-6}$alkanoyl, e.g. $C_{1-3}$alkanoyl group such as an acetyl group, or a formyl [HC(O)—], carboxamido (CONR$^{14}$R$^{15}$) or thiocarboxamido (CSNR$^{14}$R$^{15}$) group, where $R^9$ and $R^{10}$ in each instance may be the same or different and is each a hydrogen atom or an optionally substituted straight or branched $C_{1-6}$alkyl, e.g. $C_{1-3}$alkyl group such as methyl or ethyl group. Optional substituents which may be present on such R$^c$, R$^{14}$ or R$^{15}$ groups include those described below in relation to the alkyl groups R$^3$ or R$^4$.

Alkyl groups represented by $R^2$, $R^3$ or $R^4$ in compounds of formula (1) include optionally substituted straight or branched $C_{1-6}$alkyl groups, e.g. $C_{1-3}$alkyl groups such as methyl, ethyl, n-propyl or i-propyl groups. Optional substituents which may be present on these groups include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups.

Monocyclic or bicyclic aryl groups represented by the group Ar or Ar$^1$ in compounds of formula (1) include for example $C_{6-12}$ aryl groups, for example phenyl, 1-or 2-naphthyl, indenyl or isoindenyl groups. In the case of the group Ar$^1$, such groups may be optionally substituted, for example as described below.

When the monocyclic or bicyclic aryl group Ar or Ar$^1$ contains one or more heteroatoms, Ar or Ar$^1$ may be for example a $C_{1-9}$ heteroaryl group containing for example one, two, three or four heteroatoms selected from oxygen, sulphur or nitrogen atoms. In general, Ar or Ar$^1$ heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten- membered heteroaryl groups containing one, two or more heteroatoms selected from oxygen, sulphur or nitrogen atoms. Ar$^1$ heteroaryl groups of these types may be optionally substituted, for example as described below.

Examples of heteroaryl groups represented by Ar or Ar$^1$ include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b] pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar or Ar$^1$ may be attached to the remainder of the molecule of formula (1) through any ring carbon or heteroatom as appropriate. Thus, for example, when the group Ar or Ar$^1$ is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar or Ar$^1$ is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8- isoquinolinyl group.

When in compounds of formula (1) the Ar or Ar$^1$ group is a nitrogen-containing heterocycle it may be possible to form quaternary salts, for example N-alkyl quaternary salts and the invention is to be understood to extend to such salts. Thus for example when the group Ar or Ar$^1$ is a pyridyl group, pyridinium salts may be formed, for example N-alkylpyridinium salts such as N-methylpyridinium.

The aryl or heteroaryl groups represented by Ar$^1$ in compounds of formula (1) may each optionally be substituted by one, two, three or more substituents $R^{16}$. The substituent $R^{16}$ may be selected from an atom or group $R^{17}$ or —Alk(R$^{17}$)$_m$ wherein R$^{17}$ is a halogen atom, or an amino(—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk, —SO$_3$H, —SO$_2$Alk$^2$ —SO$_2$NH$_2$, —SO$_2$NHAlk, —SO$_2$N[Alk]$_2$, —CON H$_2$, —CON HAlk, CON[Alk]$_2$, —NHSO$_2$H, —NAlkSO$_2$H, —NHSO$_2$Alk, —NAlkSO$_2$Alk, —N[SO$_2$Alk]$_2$, —NHSO$_2$NH$_2$, —NAlkSO$_2$NH$_2$, —NHSO$_2$NHAlk, —NAlkSO$_2$NHAlk, —NHSO$_2$N[Alk]$_2$, —NAlkSO$_2$N[Alk]$_2$, —NHC(O)H, —NHC(O)Alk, —NAlkC(O)H, —NAlkC(O)Alk, —N[C(O)Alk]$_2$, —NHC(O)OH, —NHC(O)OAlk, —NAlkC(O)OH, —NAlkC(O)OAlk, —NHCONH$_2$, —NHCONHAlk, —NHCON[Alk]$_2$, —NAlkCON[Alk]$_2$, —NAlkCONH[Alk], —NAlkCONH$_2$, —C(S)H, —C(S)Alk, —CSNH$_2$, —CSNHAlk, —CSN[Alk]$_2$, —NHC(S)H, —NHCSAlk, —NAlkC(S)H, —NAlkC(S)Alk, —N[C(S)Alk]$_2$, —N[C(O)Alk]SO$_2$H, —NHCSNH$_2$, —NHCSNHAlk, —NHCSN[Alk]$_2$, —NAlkCSN[Alk]$_2$, —NAlkCSNHAlk, —NAlkCSNH$_2$, or —N[C(O)Alk]SO$_2$Alk group; Alk is a straight or branched C$_{1-6}$alkylene, C$_{2-6}$alkenylene, or C$_{2-6}$alkynylene chain optionally interrupted by one, two, or three —O—, or —S— atoms or —S(O)$_p$—, [where p is an integer 1 or 2] or —N(R$^b$)— groups; and m is zero or an integer 1, 2 or 3.

When in the group —Alk(R$^{17}$)$_m$ m is an integer 1, 2 or 3, it is to be understood that the substituent or substituents R$^{17}$ may be present on any suitable carbon atom in —Alk. Where more than one R$^{17}$ substituent is present these may be the same or different and may be present on the same or different carbon atom in Alk. Clearly, when m is zero and no substituent R$^{17}$ is present or when Alk forms part of a group such as —SO$_2$Alk the alkylene, alkenylene or alkynylene chain represented by Alk becomes an alkyl, alkenyl or alkynyl group.

When R$^{17}$ is a substituted amino group it may be a group —NH[Alk(R$^{17a}$)$_m$] [where Alk and m are as defined above and R$^{17}$a is as defined above for R$^{17}$ but is not a substituted amino, a substituted hydroxyl or a substituted thiol group] or a group —N[Alk(R$^{17a}$)$_m$]$_2$ wherein each —Alk(R$^{17a}$)$_m$ group is the same or different.

When R$^{17}$ is a halogen atom it may be for example a fluorine, chlorine, bromine, or iodine atom.

When R$^{17}$ is a cycloalkoxy group it may be for example a C$_{5-7}$cycloalkoxy group such as a cyclopentyloxy or cyclohexyloxy group.

When R$^{17}$ is a substituted hydroxyl or substituted thiol group it may be a group —OAlk(R$^{17a}$)$_m$ or —SAlk(R$^{17a}$)$_m$ respectively, where Alk, R$^{17a}$ and m are as just defined.

Esterified carboxyl groups represented by the group R$^{17}$ include groups of formula —CO$_2$Alk$^1$ wherein Alk$^1$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{C1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^1$ group include R$^{16}$ substituents described above.

Particular examples of the chain Alk when present include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^b$)— groups.

Particularly useful atoms or groups represented by R$^{16}$ include fluorine, chlorine, bromine or iodine atoms, or C$_{1-6}$alkyl, e.g. methyl or ethyl, C$_{1-6}$alkylamino, e.g. methylamino or ethylamino, C$_{1-6}$ hydroxyalkyl, e.g. hydroxymethyl or hydroxyethyl, C$_{1-6}$alkylthiol e.g. methylthiol or ethylthiol, C$_{1-6}$alkoxy, e.g. methoxy or ethoxy, C$_{5-7}$cycloalkoxy, e.g. cyclopentyloxy, haloC$_{1-6}$alkyl, e.g. trifluoromethyl, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, nitro, cyano, hydroxyl (—OH), formyl [HC(O)—], carboxyl (—CO$_2$H), —CO$_2$Alk$^1$ [where Alk$^1$ is as defined above], C$_{1-6}$alkanoyl e.g. acetyl, thiol (—SH), thioC$_{1-6}$alkyl, e.g. thiomethyl or thioethyl, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, C$_{1-6}$alkanoylaminoC$_{1-6}$alkyl, e.g. acetylaminomethyl or C$_{1-6}$ alkoxycarbonylamino, e.g. methoxycarbonylamino, ethoxycarbonylamino or t-butoxycarbonylamino thiocarboxamido (—CSNH$_2$), C$_{1-6}$alkylaminothiocarbonyl, e.g. methylaminothiocarbonyl or ethylaminothiocarbonyl, C$_{1-6}$dialkylaminothiocarbonyl, e.g. dimethylaminothiocarbonyl or diethylaminothiocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino, or diethylaminothiocarbonylamino, aminocarbonylC$_{1-6}$alkylamino, e.g. aminocarbonylmethylamino or aminocarbonylethylamino, aminothiocarbonylC$_{1-6}$alkylamino e.g. aminothiocarbonylmethylamino or aminothiocarbonylethylamino, formylaminoC$_{1-6}$alkylsulphonylamino, e.g. formylaminomethylsulphonylamino or formyl-aminoethylsulphonylamino, thioformylaminoC$_{1-6}$alkylsulphonylamino, e.g. thioformylaminomethylsulphonylamino or thioformylethylsulphonylamino, C$_{1-6}$acylaminosulphonylamino, e.g. acetylaminosulphonylamino, C$_{1-6}$thio-acylaminosulphonylamino, e.g. thioacetylaminosulphonylamino groups.

Where desired, two R$^{16}$ substituents may be linked together to form a cyclic group such as a cyclic ether, e.g. a C$_{2-6}$alkylenedioxy group such as ethylenedioxy.

It will be appreciated that where two or more R$^{16}$ substituents are present, these need not necessarily be the same atoms and/or groups. The $R^{16}$ substituents may be present at any ring carbon atom away from that attached to the rest of the molecule of formula (1). Thus, for example, in phenyl groups represented by Ar or $Ar^1$ any substituent may be present at the 2-, 3-, 4-, 5- or 6- positions relative to the ring carbon atom attached to the remainder of the molecule.

In the group $R^1$ in compounds of formula (1), when the group $R^{12}$ and/or $R^{13}$ is a $C_{1-3}$alkyl group it may be a straight or branched $C_{1-3}$alkyl group selected from a methyl, ethyl, n-propyl or i-propyl group. Phenyl $C_{1-3}$alkyl groups represented by the group $R^{13}$ include benzyl or phenethyl groups. These and other phenalkyl or phenyl groups represented by $R^{13}$ may be optionally substituted by one, two or more halogen atoms, e.g. chlorine, bromine, iodine or fluorine atoms or $C_{1-3}$alkyl e.g. methyl or ethyl, or $C_{1-3}$alkoxy, e.g. methoxy or ethoxy, groups.

Particular examples of $R^1$ groups include —NHC(=NCN)NHR$^{13}$, —NHC(=NCN)SR$^{13}$, —NHC(=CHNO$_2$)NHR$^{13}$ or —NHC(=CHNO$_2$)SR$^{13}$ groups, especially those wherein $R^{13}$ is a methyl, ethyl, benzyl or substituted benzyl group containing one or two halogen, $C_{1-3}$alkyl or $C_{1-3}$alkoxy substituents as just described.

In general, the groups represented by $R^1$ may be attached to the Ar group through any available ring carbon atom.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1) the group Y is preferably a —$XR^a$ group where X is —O— and $R^a$ is an optionally substituted ethyl group or, especially, an optionally substituted methyl group. Especially useful substituents which may be present on $R^a$ groups include one, two or three fluorine or chlorine atoms.

Z in the compounds of formula (1) is preferably a group $XR^5$. In compounds of this type X is especially an oxygen atom. The group $R^5$ is in particular an optionally substituted $C_{1-3}$alkyl group, especially a methyl, —CH$_2$F or —CHF$_2$ group, or a $C_{3-8}$cycloalkyl group, especially a cyclobutyl or cyclopentyl group.

Particularly useful Ar or $Ar^1$ groups in compounds of formula (1) include those groups in which Ar or $Ar^1$ is a monocyclic aryl group such as a phenyl group optionally containing one or more heteroatoms selected from oxygen, sulphur, or, in particular, nitrogen atoms. In these compounds, when the group represented by Ar or $Ar^1$ is a heteroaryl group it is preferably a nitrogen-containing monocyclic heteroaryl group, especially a six-membered nitrogen-containing heteroaryl group. Thus, in one preferred example, the groups Ar and $Ar^1$ may each be a nitrogen-containing heteroaryl group. In another preferred example Ar may be a monocyclic aryl group or a monocyclic or bicyclic heteroaryl group containing one or more oxygen, sulphur or nitrogen atoms and $Ar^1$ may be an optionally substituted six-membered nitrogen-containing $Ar^1$ heteroaryl group. In these examples, the six-membered nitrogen-containing $Ar^1$ heteroaryl group may be an optionally substituted pyridyl, pyridazinyl, pyrimidinyl, pyrazinyl or imidazolyl group. Particular examples include optionally substituted 2-pyridyl, 3-pyridyl, 5-imidazolyl, or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group, and the monocyclic or bicyclic heteroaryl group containing one or more oxygen, sulphur or nitrogen atoms may be an optionally substituted 2-furyl, 3-furyl, 2-thienyl, 3-thienyl, 2-thiazolyl, 2-benzo(b)thiophenyl, 2-benzo(b)furyl or 4-isoquinolinyl group.

In general in compounds of formula (1) when $Ar^1$ is a substituted phenyl group it may be for example a mono-, di- or trisubstituted phenyl group in which the substituent is an atom or group $R^{16}$ as defined above. When the group is a monosubstituted phenyl group the substituent may be in the 2-, or preferably 3-, or especially 4-position relative to the ring carbon atom attached to the remainder of the molecule. When the $Ar^1$ group is a disubstituted phenyl group, the substituents may be in the 2,6 position relative to the ring carbon atom attached to the remainder of the molecule.

Particularly useful substituents $R^{16}$ which may be present on $Ar^1$ groups, especially on phenyl groups, include halogen atoms or alkyl, haloalkyl, amino, substituted amino, nitro, —NHSO$_2$NH$_2$, —NHSO$_2$NHCH$_3$, —NHSO$_2$N(CH$_3$)$_2$, —NHCOCH$_3$, —NHC(O)NH$_2$, —NCH$_3$C(O)NH$_2$, —NHC(O)NHCH$_3$, —NHC(O)NHCH$_2$CH$_3$, or —NHC(O)N(CH$_3$)$_2$ groups, each of said atoms or groups being optionally separated from the remainder of the $Ar^1$ group by a group Alk as defined above.

When in compounds of formula (1) $Ar^1$ a substituted pyridyl group it may be for example a mono-or disubstituted pyridyl group, such as a mono- or disubstituted 2-pyridyl, 3-pyridyl or especially 4-pyridyl group substituted by one or two atoms or groups $R^{16}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particular class of compounds according to the invention has the formula (1) wherein Ar is a phenyl group. In compounds of this type the substituent $R^1$ may be in particular at the 3- or 4-positon relative to the phenyl carbon atom attached to the remainder of the molecule of formula (1).

In the compounds of formula (1) one preferred group of compounds are those where the group $R^2$ is a hydrogen atom; the group $R^3$ is a methyl group, or especially a hydrogen atom; the group $R^4$ is a methyl group, or especially a hydrogen atom; and Y, Z, Ar, $Ar^1$ and $R^1$ are as defined for formula (1). In compounds of this type $R^3$ and $R^4$ is each especially a hydrogen atom.

One particularly preferred group of compounds of the invention has the formula (1) wherein Y is a —$XR^a$ group, Z is a —$XR^5$ group, $R^2$, $R^3$ and $R^4$ is each a hydrogen atom, $Ar^1$ is an optionally substituted nitrogen-containing heteroaryl group, Ar is a phenyl group and $R^1$ is as defined for formula (1). In compounds of this type the group X in Y or Z is especially an oxygen atom; the group $R^a$ is especially an optionally substituted $C_{1-3}$alkyl group, particularly a methyl, —$CH_2F$, —$CH_2Cl$, —$CHF_2$, —$CHCl_2$, $CF_3$ or —$CCl_3$ group; the group $R^5$ is especially an optionally substituted $C_{1-3}$alkyl group, particularly a methyl, —$CH_2F$ or —$CHF_2$ group or a $C_{3-8}$cycloalkyl group, particularly a cyclobutyl or cyclopentyl group; and $Ar^1$ is an optionally substituted pyridyl, pyridazinyl, pyrimidinyl, pyrazinyl or imidazolyl group, especially an optionally mono- or di-substituted 2-, 3- or 4- pyridyl group. Optional substituents include those particularly described above. In general in these compounds the group $R^1$ is preferably attached to the Ar phenyl group at the 3- or 4-position relative to the phenyl carbon atom attached to the remainder of the molecule, and the group may be any of those $R^1$ groups generally or particularly described above, especially a —NHC(=NCN)$NHR^{13}$ or —NHC(=$CHNO_2$)$NHR^{13}$ group.

Particularly useful compounds according to the invention include those specifically described in the Examples hereinafter and especially include: (R)-/N{(EIZ)-1-{3-[1 -[3-Cyclopentyloxy-4-methoxyphenyl]-2-(4-pyridinyl)-ethyl]anilino}-2-nitroethenyl}-N-methylamine;

(R)-N'-Cyano-N'-{3-[1-[3-cyclopentyloxy-4-methoxyphenyl]-2-(4-pyridinyl) -ethyl]phenyl}-N-methylamine;

(R)-N-Benzyl-N"-cyano-N'-{4-[1-[3-cyclobutyloxy-4-methoxyphenyl]-2-(4-pyridinyl)ethyl]phenyl}guanidine;

(R)-N-{(EIZ)-1-{4-[1-[3,4-bis(difluoromethoxy)phenyl]-2-(4-pyridinyl)ethyl]-anilino}-2-nitroethenyl)-N-benzylamine;

R-N-{(EIZ)-1-{4-[1-[3,4-bis(difluoromethoxy)phenyl]-2-(4-pyridinyl)ethyl]-anilino}-2-nitroethenyl)-N-([4-fluorophenyl]-methyl)amine;

(R)-N-Benzyl-N'-{4-[1-[3,4-bis(difluoromethoxy)phenyl]-2-(4-pyridinyl)-ethyl]phenyl}-N"-cyanoguanidine;

(R)-N-{4-[1-[3,4-Bis(difluoromethoxy)phenyl]-2-(4-pyridinyl)-ethyl]phenyl}-N"-cyano-N-[(4-fluorophenyl)methyl]guanidine;

and the salts, solvates, hydrates, prodrugs and N-oxides thereof.

Compounds according to the invention are selective and potent inhibitors of PDE IV and advantageously have improved metabolic stability. The ability of the compounds to act in this way may be simply determined by the tests described in the Examples hereinafter.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents.

Alternatively, the active ingredient may be in powder form for constitution with a suitable vehicle, e.g. sterile pyrogen-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administratino by inhalation or insufflation.

The compounds according to the invention may be prepared by the following processes. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1991].

Thus according to a further aspect of the invention a compound of formula (1) wherein $R^1$ is a —N($R^{12}$)C(=NCN)S$R^{13}$ or —N($R^{12}$)C(=CHNO$_2$)S$R^{13}$ group may be prepared by reaction of an intermediate amine of formula (2):

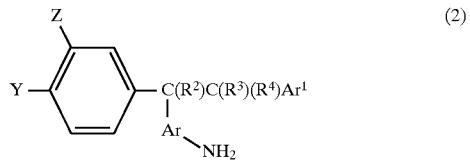

where Y, Z, $R^2$, $R^3$, $R^4$, Ar and $Ar^1$ are as defined for formula (1), with a reagent $R^{12}$ SN($R^{12}$)C(=NCN)S$R^{13}$ or $R^{16}$SN($R^{12}$)C(=CHNO$_2$)S$R^{13}$ The reaction may be performed in a solvent such as an alcohol, e.g. ethanol, or a nitrile, e.g. acetonitrile at around ambient up to the reflux temperature.

The intermediate starting materials of formula (1) may be prepared by any of the processes described in International Patent Specification Nos. WO94/14742, WO95/17386, WO95/35281 and WO95/35283 or from any appropriate compound described therein using standard procedures involving simple functional group manipulations.

In another process according to the invention, a compound of formula (1) wherein $R^1$ is a —N($R^{12}$)C(=NCN)NH$R^{13}$ or —N($R^{12}$)C(=CHNO$_2$)NH$R^{13}$ group may be prepared from a corresponding compound of formula (1) wherein $R^1$ is a —N($R^{12}$)C(=NCN)S$R^{13}$ or —N($R^{12}$)C(=CHNO$_2$)S$R^{13}$ group by reaction with an amine $R^{13}$NH.

The reaction may be performed in a solvent such as an alcohol, e.g. methanol or an ether, e.g. a cyclic ether such as tetrahydrofuran, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at around 0° to ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography.

Alternatively, a particular enantiomer may be obtained by using an appropriate chiral intermediate of formula (2) in the process described above. Chiral intermediates may be obtained in particular by use of the enantioselective process described in International Patent Specification No. WO95/17386.

A particular geometric isomer of a compound of the invention may also be obtained from a corresponding mixture of isomers using conventional separation procedures, for examples by chromatography.

The following Examples illustrate the invention. All temperatures are in ° C.

The starting anilines for the preparation of the compounds of Examples 1, 3, 5, 7 and 10 were prepared as described in International Patent Specification No. WO 95/17386 using 3-cyclopentyloxy-4-methoxybenzaldehyde, 3-cyclobutyloxy-4-methoxybenzaldehyde or 3,4-bis (difluoromethoxy)benzaldehyde as starting materials and the appropriate Grignard reagent (see the Examples in WO 95/177386)

EXAMPLE 1

(R)-3-{1-[3—Cyclopentyloxy-4-methoxyphenyl]-2-(4-[pyridinyl]ethyl}-N-[(EIZ)-1-(methylsulphanyl)-2-nitroethenyl]aniline To a solution of 3-[1-(R)-(3-cyclopentyloxy-4-methoxyphenyl)-2-(4-pyridinyl)ethyl]aniline (880 mg, 2.27 mmol) in dry acetonitrile (10 ml) at room temperature was added 1,1-bis(methylthio)-2-nitroethylene (1.20 g, 3.2 equivalents). The mixture was heated at reflux overnight and then partitioned between ethyl acetate (100 ml) and water (100 ml). The aqueous layer was separated and the organic layer washed with water (3×100 ml), brine (100 ml), dried (MgSO$_4$), filtered and solvent removed in vacuo to give a yellow foam. The foam was subjected to flash column chromatography (SiO$_2$; eluant ethyl acetate) to give the title compound as a white foam (830 mg). $^1$Hnmr (300 MHz, d$_4$ methanol). δ 1.58 (2H, br), 1.76 (6H, br), 2.38 (3H, s), 3.41 (2H, d, J 8.2 Hz), 3.75 (3H, s), 4.33 (1H, t, J 8.2 Hz), 4.71 (1H, br), 6.78 (2H, s), 6.83 (2H, s), 7.12 (1H, d, J 7.6 Hz), 7.18 (2H, d, J 6.2 Hz), 7.25 (1H, br s), 7.33 (2H, m) and 8.28 (2H, dd, J 4.5, 1.6 Hz). m/z (ESI, 40 V) 506 (MH$^+$, 100), 445 (12), 438 (10), 413 (16).

EXAMPLE 2

(R)-N-{(EIZ)-1-{3-[1-[3-Cyclopentyloxy-4-methoxyphenyl]-2-(4-pyridinyl)ethyl]anilino}-2-nitroethenyl}-N-methylamine To the compound of Example 1 (500 mg, 0.99 mmol) was added methylamine in methanol (20 ml of a 2M solution, 40 equivalents). The mixture was then heated at 40° for a period of 3 h. Solvent was removed in vacuo and the yellow residue subjected to column chromatography (SiO$_2$, eluant 23:2 dichloromethane:methanol) to give the title compound as a pale yellow solid (350 mg). $^1$Hnmr (300 MHz, d$_4$ methanol). δ 1.58 (2H, br), 1.75 (6H, br), 3.01 (2H, br), 3.41 (2H, d, J 7.5 Hz), 3.74 (3H, s), 4.34 (1H, dd, J 7.9–8.3 Hz), 4.72 (1H, br), 6.30 (1H, br), 6.77–6.85 (3H, m), 7.05 (1H, d, J 7.5 Hz), 7.17 (3H, dd, J 1.5, 3.6 Hz), 7.30–7.37 (2H, m) and 8.28 (2H, dd, J 1.5, 4.6 Hz). m/z (ES1, 40 V) 489 (MH$^+$, 100%), 421 (15), 396 (32).

EXAMPLE 3

(R)-4-{2-(3-{[Cyanoimino)(methylsulphanyl)methyl]amino}phenyl)-2-[3-cyclopentyloxy-4-methoxyphenyl]ethyl}pyridine To a solution of 3-[1-(R)-(3-cyclopentyloxy-4-methoxyphenyl)-2-(4-pyridinyl)ethyl]aniline (890 mg, 2.3 mmol) in ethanol (10 ml) at 0° was added dimethylcyanodithioimidocarbonate (1.0 g, 3equivalents). The mixture was allowed to warm to room temperature and stirred for 72 h. The mixture was partitioned between ethyl acetate (100ml) and water (100 ml), the aqueous layer was separated and the organic layer washed with water (3×50 ml), brine (50 ml), dried (MgSO$_4$), filtered and solvent removed in vacuo to give a pale yellow foam. The foam was subjected to flash column chromatography (SiO$_2$; eluant, ethyl acetate) to yield the title compound as a white foam (685 mg). $^1$Hnmr (300 MHz, CDCl$_3$). δ 1.58 (2H, br), 1.79 (6H, br), 2.44 (3H, s), 3.32 (2H, d, J 8.7 Hz), 3.80 (3H, s), 4.17 (1H, t, J 8.0 Hz), 4.66 (1H, br), 6.63 (1H, d, J 2.0 Hz), 6.79 (1H, dd, J 8.3, 2.0 Hz), 6.78 (1H, d, J 8.3 Hz), 6.96 (2H, dd, J 4.5, 1.6 Hz), 7.12 (1H, s), 7.15 (2H, s), 7.28 (2H, m) and 8.38 (2H, dd, J 4.5, 1.6 Hz).m/z (ESI, 40V) 487 (MH$^+$, 100), 445 (17), 419 (41), 377 (52).

EXAMPLE 4

(R)-N"-Cyano-N'-{3-[1-[3-cyclopentyloxy-4-methoxyphenyl]-2-(4-pyridinyl)ethyl]phenyl}-N-methylamine To the compound of Example 3 (521 mg, 1.1 mmol) was added methylamine solution in methanol (31 ml of a 2M solution, 62 mmol). The mixture was stirred at room temperature overnight, partitioned between ethyl acetate (100 ml) and water (100 ml), the aqueous layer was separated and the organic layer washed with water (2×50 ml), brine (50 ml), dried (MgSO$_4$), filtered and solvent removed in vacuo to give a crude product. This was subjected to column chromatography (SiO$_2$; eluant, 45:5, dichloromethane:methanol) to give the title compound as a white foam (320 mg). $^1$Hnmr (300 MHz, d$_4$ methanol). δ 1.58 (2H, br), 1.73 (6H, br), 2.81 (3H, s), 3.39 (2H, dd, J 1.7, 3.3 Hz), 3.74 (3H, s), 4.28 (1H, t, J 7.9 Hz), 4.72 (1H, br), 6.78 (1H, d, J 8.0 Hz), 6.81 (2H, d, J 0.9 Hz), 7.08 (1H, d, J 2.0 Hz), 7.16–7.30 (4H, m) and 8.27 (2H, d, J 5.0 Hz). m/z (ESI, 27V), 470 (MH$^+$, 100), 402 (8).

EXAMPLE 5

(R)-4-{2-(4-{[Cyanoimino)(methylsulphanyl)methyl]amino}phenyl)-2-[3-cyclobutyloxy-4-methoxyphenyl]ethyl}pyridine The title compound was prepared from 4-[1-(R)-(3-cyclobutyloxy-4-methoxyphenyl)-2-(4-pyridinyl)ethyl]aniline (2.0 g) and dimethylcyanodithioimidocarbonate (4.0 g) as a near white glass (2.63 g) using a similar procedure to the preparation of the compound of Example 3. $^1$Hnmr (CDCl$_3$) δ 1.58–1.70 (1H, br m), 1.76–1.87 (1H, br m), 2.10–2.46 (4H, br m), 2.46 (3H, s), 3.32 (2H, d, J 7.9 Hz), 3.83 (3H, s), 4.14 (1H, t, J 7.9 Hz), 4.52 (1H, p), 6.46 (1H, d, J 2.1 Hz), 6.68 (1H, dd, J 2.1, 8.3 Hz), 6.76 (1H, d, J 8.3 Hz), 6.96 (2H, d, J 5.3 Hz), 7.20 (4H, m), 8.27 (~0.75H, br s) and 8.40 (2H, d, J 5.3 Hz). m/z (ESI, 27V) 473.3 (MH$^+$, 100%).

EXAMPLE 6

(R)-N-Benzyl-N"-cyano-N'-{4-[1-[3-cyclobutyloxy-4-methoxyphenyl]-2-(4-pyridinyl)ethyl]phenyl}guanidine The title compound was prepared from the compound of Example 5 (0.5 g) and benzylamine (1.16 ml) in tetrahydrofuran (20 ml) as a white glass (0.56 g) using a similar procedure to the preparation of the compound of Example 4. 1 Hnmr (CDCl$_3$) δ 1.60–1.70 (1H, br m), 1.75–1.9 (1H, br m), 2.1–2.5 (4H, br m), 3.27 (2H, d, J 7.9 Hz), 3.81 (3H, s), 4.11 (1H, t, J 7.91 Hz), 4.47 (2H, d, J 5.4 Hz), 4.52 (1H, p (o)) 5.15 (1H, br m), 6.46 (1H, d, J 2.1 Hz), 6.66 (1H, dd, J 2.1, 8.3 Hz), 6.75 (1H, d, J 8.3 Hz), 6.90 (2H, d, J 5.5 Hz), 7.11 (2H, d, J 8.4 Hz), 7.24 (4H, br m), 7.34 (3H, br m) and 8.36 (2H, d, J 5.5 Hz). m/z (ESI 27V) 532.2 (MH$^+$, 100%).

EXAMPLE 7

(R)-4-{1-[3,4-Bis(difluoromethoxy)phenyl]-2-(4-pyridinyl)ethyl}-N'-[(EIZ)-1-(methylsulphanyl)-2-nitroethenyl]aniline To a solution of 4-[1-(R)-(3,4 bis(difluoromethoxy)phenyl)-2-(4-pyridinyl)ethyl]aniline (3.0 g, 7.4 mmol) in dry acetonitrile (30 ml) at room temperature was added 1,1-bis(methylthio)-2-nitroethylene (2.5 g, 2 equivalents). The mixture was heated at reflux overnight, cooled and the solvent removed in vacuo to give a yellow foam. The foam was subjected to flash chromatography (SiO$_2$, eluant 95% dichloromethane/5% ethanol) to give the title compound.

¹Hnmr (300 MHz CDCl₃) δ 2.36 (3H, s), 3.31 (2H, d, J 7.99 Hz), 4.25 (1H, t, J 7.94 Hz), 6.45 (1H, t, J 73.59 Hz), 6.48 (1H, t, J 73.5 Hz), 6.67 (1H, s), 6.91 (2H, d, J 6.07 Hz), 7.01–7.07 (2H, c), 7.15–7.25 (4H, c), 8.41 (2H, d, J 6.0 Hz) and 11.75 (1H, br).

EXAMPLE 8

(R)-N-{(EIZ)-1-{4-[1-[3,4-bis(difluoromethoxy)phenyl]-2-(4-pyridinyl)ethyl]anilino}-2-nitroethenyl)-N-benzylamine To a solution of the compound of Example 7 (900 mg, 1.72 mmol) in dry acetonitrile (10 ml) at room temperature was added benzylamine (900 mg, 8.4 mmol). The mixture was heated at reflux overnight, cooled and the solvent and volatiles removed in vacuo. The residue was subjected to flash chromatography (SiO₂; eluent ethyl acetate) to yield the title compound as a yellow foam (590 mg). ¹Hnmr (300 MHz CDCl₃) δ 3.3 (2H, d), 3.9 (1H, br), 4.2 (2H, m), 4.6 (1H, br), 5.1 (1H, br), 6.4 (1H, t), 6.5 (1H, t), 6.9 (2H, d), 7.0–7.5 (12H, c) and 8.4 (2H, d). m/z (ESI, 60V) 583 (MH⁺, 100), 537 (21), 490 (70), 444 (74).

The following compound was prepared using a similar procedure:

EXAMPLE 9

R-N{(EIZ)-1-{4-[1-[3,4-bis(difluoromethoxy)phenyl]-2-(4-pyridinyl)ethyl]anilino}-2-nitroethenyl)-N-([4-fluorophenyl]-methyl)amine From the compound of Example 7 (700 mg, 1.3 mmol) and 4-fluorobenzylamine (700 mg, 5.6 mmol) to yield the title compound as a yellow foam (560 mg). ¹Hnmr (300 MHz, d₄ methanol) δ 3.56 (2H, d, J 8.21 Hz), 4.49–4.55 (3H, c), 6.75 (2H, t, J 73.69 Hz), 7.09–7.27 (8H, c), 7.35–7.44 (6H, c) and 8.41 (2H, d, J 4.84). m/z (ESI, 60V), 601 (MH⁺, 100%) 508 (73), 462 (61), 314 (30).

EXAMPLE 10

(R)-4-{2-[3,4-Bis(difluoromethoxy)phenyl]-2-(4-{[(cyanoimino)(methylsulphanyl)methyl]amino}phenyl)ethyl}pyridine To a solution of 4-[1-(R)-(3,4 bis(difluoromethoxy)phenyl)-2-(4-pyridinyl)ethyl]aniline (1.8 g, 4.4 mmol) in ethanol (20 ml) at room temperature was added dimethylcyanodithioimidocarbonate (1.3 g, 8.9 mmol). The mixture was heated at 70° for 72 h, cooled and the solvent removed in vacuo to give a yellow foam. The foam was subjected to flash chromatography (SiO₂; eluant ethyl acetate) to give the title compound as a yellow foam (1.2 g). ¹Hnmr (300 MHz, CDCl₃) δ 2.46 (3H, s), 3.30 (2H, d, J 7.98 Hz), 4.23 (1H, t, J 7.84 Hz), 6.46 (1H, t, J 73.58 Hz), 6.48 (1H, t, J 73.51 Hz), 6.90 (2H, d, J 6.0 Hz), 7.02 (1H, d, J 8.38 Hz), 7.06 (1H, br), 7.16 (1H, d, J 3.0 Hz), 7.16 (1H, d, J 3.0 z), 7.18–7.25 (3H, c), 8.10 (1H, br) and 8.40 (2H, d, J 6.03 Hz).

EXAMPLE 11

(R)-N-Benzyl-N'-{4-(1-[3,4-bis(difluoromethoxy)phenyl]-2-(4-pyridinyl)ethyl]phenyl}-N"-cyanoguanidine To the compound of Example 10 (400 mg, 0.79 mmol) in anhydrous tetrahydrofuran (10 ml) was added benzylamine (1 ml, excess). The mixture was stirred at room temperature for 72 h. The solvent and volatiles were removed in vacuo to yield the title compound as a white solid (300 mg). ¹Hnmr (300 MHz, CDCl₃) δ 3.28 (2H, d, J 7.99 Hz), 4.21 (1H, t, J 7.98 Hz), 4.47 (2H, d, J 5.69 Hz), 5.27 (1H, br), 6.43 (1H, t, J 73.58 Hz), 6.47 (1H, t, J 73.39 Hz), 6.89 (2H, d, J 6.03 Hz), 6.99–7.34 (12H, c) and 8.38 (2H, d, J 6.04 Hz). For C₂₉H₂₃N₅O₇F₄ requires C, 63.94%; H, 4.47%; N, 12.43%; Found C, 63.87%; H, 4.48%; N, 12.52%.

The following compound was prepared in a similar manner:

EXAMPLE 12

(R)-N'-{4-[1-[3,4-Bis(difluoromethoxy)phenyl]-2-(4-pyridinyl)ethyl]phenyl}-N"-cyano-N-[(4-fluorophenyl)methyl]guanidine From the compound of Example 10 (400 mg, 0.79 mmol) and 4-fluorobenzylamine (1 ml, excess) as a white solid (300 mg). ¹Hnmr (300 MHz, CDCl₃) δ 3.29 (2H, d, J 8.0 Hz), 4.23 (1H, t, J 7.99 Hz), 4.43 (2H, d, J 5.67 Hz), 5.10 (1H, br), 6.44 (1H, t, J 73.57 Hz), 6.48 (1H, t, J 73.34 Hz), 6.90 (2H, d, J 5.89 Hz), 7.02–7.06 (2H, c), 7.10 (1H, br), 7.13–7.26 (8H, c) and 8.39 (2H, d, J 5.97 Hz). m/z (ESI, 60V) 582 (MH⁺, 100), 562 (21), 540 (39), 489 (15), 447 (12).

EXAMPLE 13

(R)-4-{2-[3,4-Bis(difluoromethoxy)phenyl]-2-(4-{[(cyanoimino)(4-[(fluorophenyl)methyl])methyl]amino}phenyl)ethyl}pyridine-N-oxide To the compound of Example 12 (280 mg, 0.5 mmol) in dichloromethane (5 ml) at 5° was added 50% m-chloroperbenzoic acid (170 mg, 1. equivalent). The mixture was stirred at 5° for 2 h, then quenched with saturated sodium bisulphite (2 ml). The aqueous layer was separated and the organic layer washed with saturated sodium bisulphite (3×2 ml), dried (Na₂SO₄), filtered and solvent removed in vacuo to yield the title compound as a white solid (160 mg). ¹Hnmr (300 MHz, CDCl₃) δ 3.28 (2H, d, J 8.0 Hz), 4.15 (1H, t, J 7.9 Hz), 4.44 (2H, d, J 5.78 Hz), 5.20 (1H, br), 6.48 (2H, t, J 73.43 Hz), 6.86 (2H, d, J 7.12 Hz), 6.99–7.26 (11H, c), 7.38 (1H, br) and 8.00 (2H, d, J 7.11 Hz). m/z (ESI, 60V) 598 (MH⁺, 100), 556 (82), 447 (19).

The following compound was prepared in a similar manner:

EXAMPLE 14

(R)-4-{2-(4-{[(Benzylamino)(cyanoimino)methyl]amino}phenyl)[3,4-bis(difluoromethoxy)phenyl]ethyl}pyridine-N-oxide From the compound of Example 11 (340 mg, 0.62 mmol) and 50% m-chloroperbenzoic acid as a white solid (200 mg). ¹Hnmr (300 MHz, CDCl₃) δ 3.27 (2H, d, J 8.0 Hz), 4.14 (1H, t, J 7.86 Hz), 4.48 (2H, d, J 5.72 Hz), 5.29 (1H, br), 6.48 (2H, t, J 73.49 Hz), 6.85 (2H, d, J 7.02 Hz), 7.00 (1H, dd, J 2.19, 8.43 Hz), 7.06 (1H, br), 7.12–7.34 (1OH, c), 7.50 (1H, br) and 7.98 (2H, d, J 7.03 Hz). m/z (ESI, 60V) 580 (MH⁺, 85), 538 (100), 429 (41).

The advantageous pharmacological properties of the compounds according to the invention may be demonstrated in the following in vitro and ex vivo tests:

1. Isolated Recombinant Human PDE IVA Enzyme

A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IVA, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris(hydroxymethyl)methyl]amino]-1-ethanesulphonic acid (TES) —NaOH buffer (pH 7.5), 10 mM $MgCl_2$, 0.1 μM [$^3$H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction. Results were expressed as $IC_{50}$ values.

For example, using this procedure with a recombinant PDE IVA enzyme the compounds of the Examples had $IC_{50}$ values of 3.3 nM (the compound of Example 2) and 0.5 nM (the compound of Example 4).

The compounds of the Examples had little or no activity against other isolated PDE isoenzymes (specifically PDE I, II, III or V—see WO 94/14742 for experimental details) at concentrations up to 100 μM, thus illustrating the selectivity of their action against PDE IV.

2. Rat Hepatocyte Metabolism

The improved metabolic stability of the compounds according to the invention was demonstrated in a conventional rat hepatocyte model in which rat hepatocytes were cultured in the presence of test compound. The quantity of compound remaining after a fixed period of time was then determined using mass spectroscopy.

In this test, for example, the compounds of the Examples remain substantially unmetabolised after 3 h with 80% and over of each compound remaining at the end of this period. This compares favourably with related compounds, for example compounds without any substitution present on Ar, which are extensively metabolised in 3 h.

We claim:

1. A compound of formula (1):

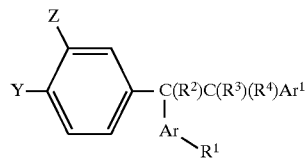

wherein:

Y is halogen or an —XR$^a$ group;

X is —O—, —S(O)$_m$— or —N(R$^b$)—, where m is zero or an integer 1 or 2;

Z is an —XR$^5$, —C(R$^6$)=C(R$^7$)(R$^8$) or —(CHR$^6$), CH(R$^7$)(R$^8$) group, where n is zero or the integer 1;

each of R$^a$ and R$^b$ is independently hydrogen or an optionally substituted alkyl group;

R$^1$ is an —N(R$^{12}$)C(=NCN)NHR$^{13}$, —N(R$^{12}$)C(=NCN)SR$^{13}$, —N(R$^{12}$)C(=CHNO$_2$)NHR$^{13}$ or —N(R$^{12}$)C(=CHNO$_2$)SR$^{13}$ group;

R$^2$ is hydrogen, fluorine, hydroxyl or an optionally substituted alkyl group;

R$^3$ is hydrogen, fluorine or an optionally substituted alkyl group;

R$^4$ is hydrogen, fluorine, an optionally substituted alkyl group, an alkoxyalkyl, alkanoyl, formyl, carboxamido or thiocarboxamido group or —OR$^c$, where R$^c$ is hydrogen or an optionally substituted alkyl or alkenyl group;

R$^5$ is an optionally substituted alkyl, alkenyl, cycloalkyl, cycloalkenyl or heterocycloalkyl group;

R$^6$ is hydrogen, fluorine or a methyl group;

each of R$^7$ and R$^8$ is independently hydrogen, fluorine, —CN, NO$_2$, or an optionally substituted alkyl, alkenyl, alkoxy, alkylthio, —CO$_2$R$^9$, —CONR$^{10}$R$^{11}$ or —CSNR$^{10}$R$^{11}$ group, or R$^7$ and R$^8$, together with the carbon atom to which they are attached, are linked to form an optionally substituted cycloalkyl, cycloalkenyl or heterocycloalkyl group;

each of R$^9$, R$^{10}$ and R$^{11}$ is independently hydrogen or an optionally substituted alkyl, aralkyl or aryl group;

R$^{12}$ is hydrogen or a C$_{1-3}$alkyl group;

R$^{13}$ is hydrogen, a C$_{1-3}$alkyl group, an optionally substituted phenyl group or an optionally substituted phenylC$_{1-3}$alkyl group;

Ar$^1$ is an optionally substituted monocyclic or bicyclic aryl group, optionally containing one or more heteroatoms selected from oxygen, sulphur and nitrogen atoms; and Ar is a monocyclic or bicyclic aryl group, optionally containing one or more heteroatoms selected from oxygen, sulphur and nitrogen atoms;

or a salt, solvate, hydrate, prodrug or N-oxide thereof.

2. A compound according to claim 1 wherein each of R$^2$, R$^3$ and R$^4$ is a hydrogen atom, Y is a —XR$^a$ group, Z is a —XR$^5$ group, Ar$^1$ is an optionally substituted nitrogen-containing heteroaryl group and Ar is a phenyl group.

3. A compound according to claim 2 wherein Y is an —OR$^a$ group where R$^a$ is an optionally substituted C$_{1-3}$alkyl group, and Z is an —OR$^5$ group where R$^5$ is an optionally substituted C$_{1-3}$alkyl group or a C$_{3-8}$cycloalkyl group.

4. A compound according to claim 2 wherein Ar$^1$ is an optionally substituted pyridyl, pyridazinyl, pyrimidinyl, pyrazinyl or imidazolyl group.

5. A compound according to claim 4 wherein Ar$^1$ is an optionally mono- or di-substituted 2-, 3- or 4- pyridyl group.

6. A compound according to claim 1 wherein R$^1$ is a —NHC(=NCN)NHR$^{13}$ or —NHC(=CHNO$_2$)NHR$^{13}$ group.

7. A compound according to claim 6 wherein R$^{13}$ is a methyl, ethyl, benzyl or substituted benzyl group containing one or two halogen, C$_{1-3}$alkyl or C$_{1-3}$alkoxy substituents.

8. A compound which is:

(R)-N[{(EIZ)-1-{3-[1-[3—Cyclopentyloxy-4-methoxyphenyl]-2-(4-pyridinyl) ethyl]anilino}-2-nitroethenyl}-N-methylamine;

(R)-N'-Cyano-N'-{3-[1-[3-cyclopentyloxy-4-methoxyphenyl]-2-(4-pyridinyl)ethyl]phenyl}-N-methylamine;

(R)-N-Benzyl- N"-cyano-N'-{4-[ 1-[3-cyclobutyloxy-4-methoxyphenyl]-2-(4-pyridinyl)ethyl]phenyl}guanidine;

(R)-N-(EIZ)-1-{4-[1-[3,4-bis(difluoromethoxy)phenyl]-2-(4-pyridinyl)ethyl]anilino}-2-nitroethenyl)-N-benzylamine;

R-N-{(EIZ)-1-{4-[1-[3,4-bis(difluoromethoxy)phenyl]-2-(4-pyridinyl)ethyl]anilino}-2-nitroethenyl)-N-([4-fluorophenyl]-methyl)amine;

(R)-N-Benzyl-N'-{4-[1-[3,4-bis(difluoromethoxy)phenyl]-2-(4-pyridinyl)-ethyl]phenyl}-N"-cyanoguanidine;

(R)-M-{4-[1-[3,4-Bis(difluoromethoxy)phenyl]-2-(4-pyridinyl)ethyl]-phenyl}-N"-cyano-N-[(4-fluorophenyl)methyl]guanidine;

and the salts, solvates, hydrates, prodrugs and N-oxides thereof.

9. A compound of formula (1):

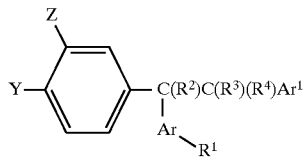

wherein:

Y is an —XR$^a$ group;

X is —O—, —S(O)$_m$— or —N(R$^b$)—, where m is zero or an integer 1 or 2;

Z is an —XR$^5$ group;

each of R$^a$ and R$^b$ is independently hydrogen or an optionally substituted alkyl group;

R$^1$ is an —N(R$^{12}$)C(=NCN)NHR$^{13}$, —N(R$^{12}$)C(=NCN)SR$^{13}$, —N(R$^{12}$)C(=CHNO$_2$)NHR$^{13}$ or —N(R$^{12}$)C(=CHNO$_2$)SR$^{13}$ group;

R$^2$, R$^3$ and R$^4$ are hydrogen;

R$^5$ is an optionally substituted alkyl, alkenyl, cycloalkyl, cycloalkenyl or heterocycloalkyl group;

R$^{12}$ is hydrogen or a C$_{1-3}$alkyl group;

R$^{13}$ is hydrogen, a C$_{1-3}$alkyl group, an optionally substituted phenyl group or an optionally substituted phenylC$_{1-3}$alkyl group;

Ar$^1$ is an optionally substituted nitrogen-containing heteroaryl group; and

Ar is a phenyl group;

or a salt, solvate, hydrate, prodrug or N-oxide thereof.

10. A compound according to claim 9 wherein X is —O—, R$^a$ is an optionally substituted C$_{1-3}$alkyl group, R$^5$ is an optionally substituted C$_{1-3}$alkyl group or a C$_{3-8}$-cycloalkyl group, Ar$^1$ is an optionally substituted pyridyl, pyridazinyl, pyrimidinyl, pyrazinyl or imidazolyl group, and R$^1$ is an —NHC(=NCN)NHR$^{13}$ or —NHC(=CHNO$_2$)NHR$^{13}$ group.

11. A compound according to claim 10 wherein R$^a$ is a methyl, —CH$_2$F, —CH$_2$Cl, —CHF$_2$, —CHCl$_2$, —CF$_3$ or —CCl$_3$ group, R5 is a methyl, —CH$_2$F, —CHF$_2$, cyclobutyl or cyclopentyl group and Ar$^1$ is an optionally mono- or di-substituted 2-, 3- or 4-pyridyl group.

12. A compound according to claim 8 which is (R)-N-Benzyl-N"-cyano-N"-{4-[1-[3-cyclobutyloxy-4-methoxyphenyl]-2-(4-pyridinyl)ethyl]phenyl)}guanidine; or a salt, solvate, hydrate, prodrug or N-oxide thereof.

13. A pharmaceutical composition comprising a compound of formula (1):

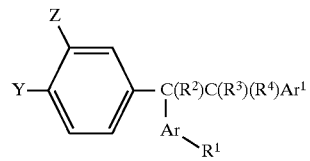

wherein:

Y is halogen or an —XR$^a$ group;

X is —O—, —S(O)$_m$— or —N(R$^b$)—, where m is zero or an integer 1 or 2;

Z is an —XR$^5$, —C(R$^6$)=C(R$^7$(R$^8$) or —(CHR$^6$)$_n$CH(R$^7$)(R$^8$) group, where n is zero or the integer 1;

each of R$^a$ and R$^b$ is independently hydrogen or an optionally substituted alkyl group;

R$^1$ is an —N(R$^{12}$)C(=NCN)NHR$^{13}$, —N(R$^{12}$)C(=NCN)SR$^{13}$, —N(R$^{12}$)C(=CHNO$_2$)NHR$^{13}$ or —N(R$^{12}$)C(=CHNO$_2$)SR$^{13}$ group;

R$^2$ is hydrogen, fluorine, hydroxyl or an optionally substituted alkyl group;

R$^3$ is hydrogen, fluorine or an optionally substituted alkyl group;

R$^4$ is hydrogen, fluorine, an optionally substituted alkyl group, an alkoxyalkyl, alkanoyl, formyl, carboxamido or thiocarboxamido group or —OR$^c$, where R$^c$ is hydrogen or an optionally substituted alkyl or alkenyl group;

R$^5$ is an optionally substituted alkyl, alkenyl, cycloalkyl, cycloalkenyl or heterocycloalkyl group;

R$^6$ is hydrogen, fluorine or a methyl group;

each of R$^7$ and R$^8$ is independently hydrogen, fluorine, —CN, NO$_2$, or an optionally substituted alkyl, alkenyl, alkoxy, alkylthio, —CO$_2$R$^9$, —CONR$^{10}$R$^{11}$ or —CSNR$^{10}$R$^{11}$ group, or R$^7$ and R$^8$, together with the carbon atom to which they are attached, are linked to form an optionally substituted cycloalkyl, cycloalkenyl or heterocycloalkyl group;

each of R$^9$, R$^{10}$ and R$^{11}$ is independently hydrogen or an optionally substituted alkyl, aralkyl or aryl group;

R$^{12}$ is hydrogen or a C$_{1-3}$alkyl group;

R$^{13}$ is hydrogen, a C$_{1-3}$alkyl group, an optionally substituted phenyl group or an optionally substituted phenylC$_{1-3}$alkyl group;

Ar$^1$ is an optionally substituted monocyclic or bicyclic aryl group, optionally containing one or more heteroatoms selected from oxygen, sulphur and nitrogen atoms; and Ar is a monocyclic or bicyclic aryl group, optionally containing one or more heteroatoms selected from oxygen, sulphur and nitrogen atoms;

or a salt, solvate, hydrate, prodrug or N-oxide thereofl together with one or more pharmaceutically acceptable carriers, excipients or diluents.

14. A method of preventing or treating an inflammatory disease in a patient comprising administering to the patient, in an amount effective to elevate intracellular levels of adenosine 3',5'-cyclic monophosphate (cAMP), a composition which comprises a selective inhibitor of a phosphodiesterase (PDE) IV isoenzyme selected from a compound according to claim 1 and a pharmaceutically acceptable carrier, excipient or diluent.

15. A method according to claim 14 wherein said inflammatory disease is asthma.

16. A method according to claim 14 wherein said inflammatory disease is selected from the group consisting of inflammatory airway disease, chronic bronchitis, eosinophilic granuloma, cellular proliferative disorders, endotoxic shock, septic shock, ulcerative colitis. Crohn's disease, reperfusion injuries, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis, artherosclerosis, rheumatoid arthritis, osteoarthritis, alkylosing spondylitis, transplant rejection and graft versus host disease.

* * * * *